US006764504B2

(12) United States Patent
Wang et al.

(10) Patent No.: US 6,764,504 B2
(45) Date of Patent: Jul. 20, 2004

(54) COMBINED SHAPED BALLOON AND STENT PROTECTOR

(75) Inventors: Lixiao Wang, Maple Grove, MN (US); John Jianhua Chen, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 89 days.

(21) Appl. No.: 09/754,661

(22) Filed: Jan. 4, 2001

(65) Prior Publication Data

US 2002/0120320 A1 Aug. 29, 2002

(51) Int. Cl.[7] ........................... A61F 2/06; A61M 29/02
(52) U.S. Cl. ..................................... 623/1.11; 606/194
(58) Field of Search ............................ 623/1.11, 1.12, 623/1.15; 606/194, 195, 191, 192, 198, 108; 604/96.01, 104

(56) References Cited

U.S. PATENT DOCUMENTS

| | | | |
|---|---|---|---|
| 4,580,568 A | 4/1986 | Gianturco | 128/345 |
| 4,649,922 A | 3/1987 | Wiktor | 128/344 |
| 4,655,771 A | 4/1987 | Wallsten | 623/1 |
| 4,681,110 A | 7/1987 | Wiktor | 128/343 |
| 4,705,517 A | 11/1987 | DiPisa, Jr. | 128/325 |
| 4,733,665 A | 3/1988 | Palmaz | 128/343.344 |
| 4,740,207 A | 4/1988 | Kreamer | 623/1 |
| 4,760,849 A | 8/1988 | Kropf | 128/341 |
| 4,776,337 A | 10/1988 | Palmaz | 128/343 |
| 4,795,458 A | 1/1989 | Regan | 623/1 |
| 4,800,882 A | 1/1989 | Gianturco | 128/343 |
| 4,830,003 A | 5/1989 | Wolff et al. | 128/343 |
| 4,856,516 A | 8/1989 | Hillstead | 128/343 |
| 4,877,030 A | 10/1989 | Beck et al. | 128/343 |
| 4,886,062 A | 12/1989 | Wiktor | 128/343 |
| 4,907,336 A | 3/1990 | Gianturco | 29/515 |
| 4,913,141 A | 4/1990 | Hillstead | 606/108 |
| 4,922,905 A | 5/1990 | Strecker | 606/195 |
| 4,923,464 A | 5/1990 | DiPisa, Jr. | 606/195 |
| 4,950,227 A | 8/1990 | Savin et al. | 604/8 |
| 4,954,126 A | 9/1990 | Wallsten | 600/36 |
| 4,969,890 A | 11/1990 | Sugita et al. | 606/192 |
| 4,990,151 A | 2/1991 | Wallsten | 606/108 |
| 4,990,155 A | 2/1991 | Wilkoff | 606/191 |
| 4,994,071 A | 2/1991 | MacGregor | 606/194 |
| 5,007,926 A | 4/1991 | Derbyshire | 623/1 |
| 5,019,090 A | 5/1991 | Pinchuk | 606/194 |
| 5,035,706 A | 7/1991 | Giantureo et al. | 606/198 |
| 5,041,126 A | 8/1991 | Gianturco | 606/195 |
| 5,059,211 A | 10/1991 | Stack et al. | 606/198 |
| 5,061,275 A | 10/1991 | Wallsten et al. | 623/1 |
| 5,064,435 A | 11/1991 | Porter | 623/12 |
| 5,078,726 A | 1/1992 | Kreamer | 606/194 |
| 5,089,006 A | 2/1992 | Stiles | 606/198 |
| 5,092,841 A | 3/1992 | Spears | 604/96 |

(List continued on next page.)

FOREIGN PATENT DOCUMENTS

EP 0540858 A1 5/1993

*Primary Examiner*—Peter Nerbun
(74) *Attorney, Agent, or Firm*—Vidas, Arrett & Steinkraus, P.A.

(57) ABSTRACT

A stent delivery catheter comprising a catheter shaft and balloon engaged thereto. The balloon being inflatable from a first inflation state to a first expanded state as well as to a second expanded state. The balloon having a stent mounting region for retaining and delivery of a stent therefrom, and at least one adjacent region. The stent mounting region having a first diameter and the at least one adjacent region having a second diameter. In the first inflation state the first diameter being less than the second diameter. In the first expanded state the first diameter being no greater than the second diameter. In the second expanded state the first diameter being greater than the second diameter. The stent being retained on the stent mounting region by engagement of the at least one adjacent portion and at least one retractable stent retaining sleeve.

32 Claims, 14 Drawing Sheets

U.S. PATENT DOCUMENTS

| | | | |
|---|---|---|---|
| 5,092,877 A | 3/1992 | Pinchuk | 623/1 |
| 5,104,399 A | 4/1992 | Lazarus | 623/1 |
| 5,104,404 A | 4/1992 | Wolff | 414/92 |
| 5,108,416 A | 4/1992 | Ryan et al. | 606/194 |
| 5,108,417 A | 4/1992 | Sawyer | 606/198 |
| 5,116,309 A | 5/1992 | Coll | 604/8 |
| 5,116,318 A | 5/1992 | Hillstead | 604/96 |
| 5,116,360 A | 5/1992 | Pinchuk et al. | 623/1 |
| 5,122,154 A | 6/1992 | Rhodes | 606/198 |
| 5,123,917 A | 6/1992 | Lee | 623/1 |
| 5,133,732 A | 7/1992 | Wiktor | 604/104 |
| 5,135,536 A | 8/1992 | Hillstead | 606/195 |
| 5,147,385 A | 9/1992 | Beck et al. | 623/1 |
| 5,163,952 A | 11/1992 | Froix | 623/1 |
| 5,171,262 A | 12/1992 | MacGregor | 623/1 |
| 5,192,297 A | 3/1993 | Hull | 606/195 |
| 5,195,984 A | 3/1993 | Schatz | 606/198 |
| 5,234,457 A | 8/1993 | Anderson | 606/198 |
| 5,282,824 A | 2/1994 | Gianturco | 606/198 |
| 5,292,331 A | 3/1994 | Boneau | 606/108 |
| 5,403,341 A | 4/1995 | Solar | 606/108 |
| 5,447,497 A | 9/1995 | Sogard et al. | 604/101 |
| 5,470,313 A | 11/1995 | Crocker et al. | 604/96 |
| 5,556,383 A | 9/1996 | Wang et al. | 604/96 |
| 5,632,760 A | 5/1997 | Shelban et al. | 606/191 |
| 5,645,560 A | 7/1997 | Crocker et al. | 606/192 |
| 5,738,901 A | 4/1998 | Wang et al. | 427/2.3 |
| 5,749,851 A | 5/1998 | Wang | 604/96 |
| 5,836,965 A | 11/1998 | Jendersee et al. | 606/198 |
| 5,843,116 A | 12/1998 | Crocker et al. | 606/192 |
| 5,968,069 A * | 10/1999 | Dusbabek et al. | 604/194 |
| 5,980,532 A | 11/1999 | Wang | 606/108 |
| 6,024,752 A | 2/2000 | Horn et al. | 606/192 |
| 6,048,350 A | 4/2000 | Vrba | 606/108 |
| 6,120,523 A | 9/2000 | Crocker et al. | 606/192 |
| 6,383,212 B2 * | 5/2002 | Durcan et al. | 623/1.11 |
| 6,409,741 B1 | 6/2002 | Crocker et al. | 606/192 |
| 2003/0028211 A1 | 2/2003 | Crocker et al. | 606/192 |

* cited by examiner

COMBINED SHAPED BALLOON AND STENT PROTECTOR

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates generally to a method of installing a stent utilizing a balloon catheter to perform an initial angioplasty and to seat the stent after it has been located in the vessel. The invention also relates to novel balloon structures which have particular use in the method of the invention. More specifically, this invention relates to a stent delivery system wherein at least a portion of the balloon is step compliant which provides the balloon with the ability to expand specific portions of the balloon at different times according to a variety of inflation pressures. In addition the unique shape of the balloon may be configured to engage the stent throughout the insertion as well as the delivery procedures which in turn reduces longitudinal movement of an associated medical device such as a stent, stent-graft, graft or vena cava filter mounted on the balloon both prior to and during balloon expansion.

2. Description of the Related Art

Expandable, implantable medical devices such as stents are utilized in a number of medical procedures and situations as are stent delivery assemblies. As such, their structure and function are well known. A stent is a generally cylindrical prosthesis introduced via a catheter into a lumen of a body vessel in a configuration having a generally reduced diameter and then expanded to the diameter of the vessel. The stent may be self-expanding, such as a NITINOL shape memory stent, or it may be expandable by means of an inflatable portion of the catheter, such as a balloon. In its expanded configuration, the stent supports and reinforces the vessel walls while maintaining the vessel in an open, unobstructed condition.

Self-expanding, inflation assisted expandable and inflation expandable stents are well known and widely available in a variety of designs and configurations. Inflation expandable and inflation assisted expandable stents are expanded via outward radial pressure such as that provided by a balloon disposed underneath the stent during inflation of the balloon.

Medical device delivery balloons may have a variety of shapes, sizes, inflation characteristics and a variety of other performance attributes. Some examples of balloons which may be used for the expansion and delivery of a medical device are described in U.S. Pat. Nos. 5,556,383; 5,738,901; 6,024,752; and 6,048,350.

In advancing an inflation expandable stent through a body vessel to the deployment site, there are a number of important considerations. The stent must be able to securely maintain its axial position on the delivery catheter, without translocating proximally or distally, and especially without becoming separated from the catheter. Furthermore, it may be desirable to protect the distal and proximal ends of the stent to prevent distortion of the stent and to prevent abrasion and/or to reduce potential trauma to the vessel walls.

To address the concerns stated above, one approach has been identified which utilizes a retractable sheath or sheaths which are disposed about the distal end of the catheter and cover the stent and balloon. In such devices the sheath is retracted prior to the inflation of the balloon and subsequent delivery of the stent. Another solution involves the utilization of one or more stent retaining means such as elastomeric sleeves or socks. The socks are disposed about the ends of the stent and the respective adjacent portions of the catheter shaft. Socks may be constructed such that during balloon inflation the socks release the stent as a result of the forces and change in geometry resulting from the expanding balloon. It is also known that socks may be constructed to retract or be pulled off of the stent as a result of their construction and the expansion of the balloon.

Inflation expandable stent delivery and deployment assemblies are known which utilize restraining means that overlie the stent during delivery. U.S. Pat. No. 4,950,227 to Savin et al., relates to an inflation expandable stout delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site. The content of all references, including patents and patent applications are respectively incorporated it their entirety heroin by reference.

Providing a means for containing and securing the stent or other medical device on the balloon catheter prior to inflation is but one problem facing stent delivery systems. An additional concern is the shifting or sliding of the stent relative to the balloon during balloon expansion. Numerous attempts have been made to reduce or prevent translocation of the stent on the balloon during balloon expansion. For example: copending U.S. patent application Ser. No. 09/667,916, filed Sep. 22, 2000 and entitled *Coated Stents with Better Gripping Ability*, describes a stent coating which provides the stent with improved ability to adhere to the balloon during the expansion process. Another example is U.S. Pat. No. 5,836,965 which describes a process wherein a balloon is expanded and heat set then allowed to cool in order to adhere the balloon to the stent. Yet another example is co-pending U.S. patent application Ser. No. 08/740,727, filed Nov. 1, 1996 and entitled *Selective Coating Of A Balloon Catheter With Lubricous Material For Stent Deployment*, which describes a balloon having a tacky coating for securing a stent to a balloon prior to delivery.

Angioplasty, an accepted and well known medical practice involves inserting a balloon catheter into the blood vessel of a patient, maneuvering and steering the catheter through the patient's vessels to the site of the lesion with the balloon in an uninflated form. The uninflated balloon portion of the catheter is located within the blood vessel such that it crosses the lesion or reduced area. Pressurized inflation fluid is metered to the inflatable balloon through a lumen formed in the catheter to thus dilate the restricted area. The inflation fluid is generally a liquid and is applied at relatively high pressures, usually in the area of six to twenty atmospheres. As the balloon is inflated it expands and forces open the previously closed area of the blood vessel. Balloons used in angioplasty procedures such as this are generally fabricated by molding and have predetermined design dimensions such as length, wall thickness and nominal diameter. Balloon catheters are also used in other systems of the body for example the prostate and the urethra. Balloon catheters come in a large range of sizes and must be suitably dimensioned for their intended use.

Recently the use of a catheter delivered stent to prevent an opened lesion from reclosing or to reinforce a weakened vessel segment, such as an aneurism, has become a common procedure. A typical procedure for stent installation involves performing an initial angioplasty to open the vessel to a predetermined diameter sufficient to permit passage of a stent delivery catheter across the lesion, removal of the angioplasty balloon catheter, insertion of a delivery catheter carrying the stent and a stent deploying mechanism, deploying the stent across the opened lesion so as to separate the stent from the catheter and bring it into contact with the vessel wall, usually with dilation to a lager diameter using a balloon larger than the balloon of the predilation catheter, and then removing the delivery catheter (after deflating the balloon if used). In many cases it has become the practice to then "retouch" the dilation by deploying a third catheter carrying a balloon capable of dilating at a substantially higher pressure to drive the stent into the vessel wall, thereby to assure that there is no risk of the stent later shifting its position and to reduce occurrence of restenosis or thrombus formation. This third "retouch" dilation is often considered necessary when the balloon used to seat the stent is made of a compliant material because such balloons generally cannot be safely pressurized above 9–12 atm., and higher pressures are generally considered necessary to assure full uniform lesion dilation and seating of the stent.

A wide variety of stent configurations and deployment methods are known. For instance, stent configurations include various forms of bent wire devices, self-expanding stents; stents which unroll from a wrapped configuration on the catheter; and stents which are made of a deformable material so that the device may be deformed on deployment from a small diameter to a larger diameter configuration. References disclosing stent devices and deployment catheters include:

| U.S. Pat. No. 4733665 | Palmaz |
| U.S. Pat. No. 4776337 | Palmaz |
| U.S. Pat. No. 5195984 | Schatz |
| U.S. Pat. No. 5234457 | Andersen |
| U.S. Pat. No. 5116360 | Pinchuck et al |
| U.S. Pat. No. 5116318 | Hillstead |
| U.S. Pat. No. 4649922 | Wiktor |
| U.S. Pat. No. 4655771 | Wallsten |
| U.S. Pat. No. 5089006 | Stiles |
| U.S. Pat. No. 5007926 | Derbyshire |
| U.S. Pat. No. 4705517 | DiPisa, Jr. |
| U.S. Pat. No. 4740207 | Kreamer |
| U.S. Pat. No. 4877030 | Beck et al |
| U.S. Pat. No. 5108417 | Sawyer |
| U.S. Pat. No. 4923464 | DiPisa, Jr |
| U.S. Pat. No. 5078726 | Kreamer |
| U.S. Pat. No. 5171262 | MacGregor |
| U.S. Pat. No. 5059211 | Stack et al |
| U.S. Pat. No. 5104399 | Lazarus |
| U.S. Pat. No. 5104404 | Wolff |
| U.S. Pat. No. 5019090 | Pinchuk |
| U.S. Pat. No. 4954126 | Wallsten |
| U.S. Pat. No. 4994071 | MacGregor |
| U.S. Pat. No. 4580568 | Gianturco |

-continued

| U.S. Pat. No. 4681110 | Wiktor |
| U.S. Pat. No. 4800882 | Gianturco |
| U.S. Pat. No. 4830003 | Wolff et al |
| U.S. Pat. No. 4856516 | Hillstead |
| U.S. Pat. No. 4922905 | Strecker |
| U.S. Pat. No. 4886062 | Wiktor |
| U.S. Pat. No. 4907336 | Gianturco |
| U.S. Pat. No. 4913141 | Hillstead |
| U.S. Pat. No. 5092877 | Pinchuk |
| U.S. Pat. No. 5123917 | Lee |
| U.S. Pat. No. 5116309 | Coll |
| U.S. Pat. No. 5122154 | Rhodes |
| U.S. Pat. No. 5133732 | Wiktor |
| U.S. Pat. No. 5135536 | Hillstead |
| U.S. Pat. No. 5282824 | Gianturco |
| U.S. Pat. No. 5292331 | Boneau |
| U.S. Pat. No. 5035706 | Gianturco et al |
| U.S. Pat. No. 5041126 | Gianturco |
| U.S. Pat. No. 5061275 | Wallsten et al |
| U.S. Pat. No. 5064435 | Porter |
| U.S. Pat. No. 5092841 | Spears |
| U.S. Pat. No. 5108416 | Ryan et al |
| U.S. Pat. No. 4990151 | Wallsten |
| U.S. Pat. No. 4990155 | Wilkoff |
| U.S. Pat. No. 4969890 | Sugita et al |
| U.S. Pat. No. 4795458 | Regan |
| U.S. Pat. No. 4760849 | Kropf |
| U.S. Pat. No. 5192297 | Hull |
| U.S. Pat. No. 5147385 | Beck et al |
| U.S. Pat. No. 5163952 | Froix |

In U.S. Pat. No. 5,348,538, the entire contents of which being incorporated herein by reference, there is described a single layer balloon which follows a stepped compliance curve. The stepped compliance curves of these balloons has a lower pressure segment following a first generally linear profile, a transition region, typically in the 8–14 atm range, during which the balloon rapidly expands yielding in elastically, and a higher pressure region in which the balloon expands along a generally linear, low compliance curve. The stepped compliance curve allows a physician to dilate different sized lesions without using multiple balloon catheters.

Stepped compliance curve catheter balloon devices using two different coextensively mounted balloon portions of different initial inflated diameter, are also described in U.S. Pat. No. 5,447,497 and in U.S. Pat. No. 5,358,487 to Miller. These dual layer balloons are designed with the outer balloon portion larger than the inner portion so that the compliance curve follows the inner balloon portion until it reaches burst diameter and then, after the inner balloon bursts, the outer balloon becomes inflated and can be expanded to a larger diameter than the burst diameter of the inner balloon.

A polyethylene ionomer balloon with a stepped compliance curve is disclosed in EP 540 858. The reference suggests that the balloon can be used on stent delivery catheters. The disclosed balloon material of this reference, however, yields a compliant balloon and therefore a stent delivered with such a balloon would typically require "retouch."

Balloons having a stepped compliance curve have also been described for use in stent delivery. Two examples of such stent delivery balloons and methods of their use are described in U.S. Pat. No. 5,749,851 and U.S. Pat. No. 5,980,532, respectively incorporated in their entirety herein by reference.

The entire content of all of the patents and patent applications listed within the present patent application are respectively incorporated in their entirety herein by reference.

BRIEF SUMMARY OF THE INVENTION

The invention in one aspect is directed to a medical balloon. More specifically, the present invention is directed to a stent delivery system employing a unique stepped compliant balloon which is shaped to retain a stent about a stent mounting region of the balloon prior to and during stent delivery. The balloon is capable of providing low pressure predilation at a relatively small diameter to open the lesion sufficiently to allow insertion and deployment of the stent across the lesion and for subsequent high pressure embedding of the stent in the vessel wall. The same balloon catheter may also be employed to insert and deploy the stent. Thus at least one catheter may be eliminated from what may otherwise be a two or three catheter installation process.

In at least one embodiment of the invention, the balloon of the invention may be made by molding a balloon into a configuration in which the second portion has a larger diameter than the first portion and then shrinking the second portion to the diameter of the first portion or less than the diameter of the first portion. The method of making such balloons comprises yet another aspect of the invention.

In at least one embodiment of the invention, the balloon may be incorporated into a stent delivery catheter, wherein a stent mounting region of the balloon has a diameter less than the diameter of the balloon ends, whereby the stent is prevented from longitudinal migration relative to the catheter as a result of interference provided by the balloon ends. The balloon may be configured to expand so that the stent remains held in place during balloon expansion.

In at least one embodiment of the invention the balloon is configured to have a first inflation state, a second inflation state, and a third or fully inflated state.

In yet another embodiment of the invention the balloon may be configured to expand such that the balloon ends maintain a larger diameter than the stent mounting region until a predetermined inflation pressure is achieved, whereupon the stent mounting region may expand to a diameter greater than the diameter of the balloon ends.

In yet another aspect of the invention a stent delivery catheter may employ a stepped compliant balloon and one or more stent retaining sleeves. The balloon may be configured such that the balloon ends inflate sufficiently to cause the sleeves to retract, whereupon the stent mounting region expands to release the stent.

These and other more detailed and specific objectives and an understanding of the invention will become apparent from a consideration of the following Detailed Description of the Invention in view of the Drawings. Other embodiments may also be apparent, but which are not described in detail, from the following description.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

The catheters employed in the practice of the present invention are most conveniently constructed as over-the-wire balloon catheters of conventional form for use in angioplasty, except that the balloon has a stepped compliance curve. However it should be understood that the present invention can be applied, in addition to over-the-wire catheters, to fixed-wire catheters, to shortened guide wire lumens or single operator exchange catheters, and to non over-the-wire balloon catheters. Furthermore this invention can be used with balloon catheters intended for use in any and all vascular systems of cavities of the body.

Figure 1:
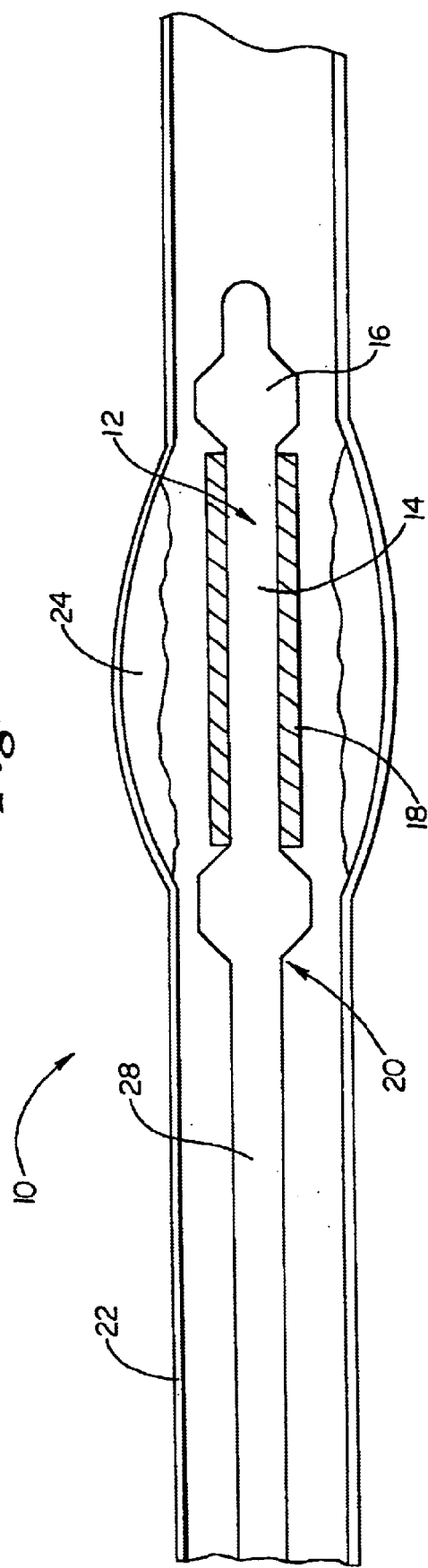
FIG. 1 is a side view of an embodiment of the invention as depicted within a body vessel.

As may be seen in FIG. 1, the present invention is directed to a stent delivery catheter, indicated generally at 10, which employs a balloon 12 which is mounted to a distal portion 20 of the catheter shaft 28. In the present invention, the balloon 12 includes a stent mounting region 14 and a pair of adjacent end portions 16.

A stent 18 is disposed about the stent mounting region 14 prior to stent delivery. The stent 18 is delivered by advancing the distal portion 20 of the catheter 10 through a body lumen or vessel 22 to a legion site 24. The balloon 12 is then inflated to predetermined pressure to expand the stent to a fully expanded state.

As is know to those of skill in the art, when a medical balloon of catheter is in the non-inflated state, the balloon will typically include one or more folds. The folded configuration of the balloon provides numerous benefits to the catheter device. An example of a folded balloon is described in U.S. patent application Ser. No. 09/335,361, filed Jun. 17, 1999 and entitled *Stent Securement By Balloon Modification*, the entire contents of which being incorporated herein by reference. The balloon 12 depicted in FIG. 1 is shown in what is referred to herein as the first inflation state. However, the first inflation state is considered for purposes of this application to be an inflation state wherein the balloon 12 has been unfolded by an internal inflation pressure of about 1 to about 3 atmospheres. Despite, being "unfolded" by such pressure, the balloon 12 as shown in FIG. 1 is not yet expanded and is thus may be characterized as being unexpanded or nominally inflated.

Figure 2:
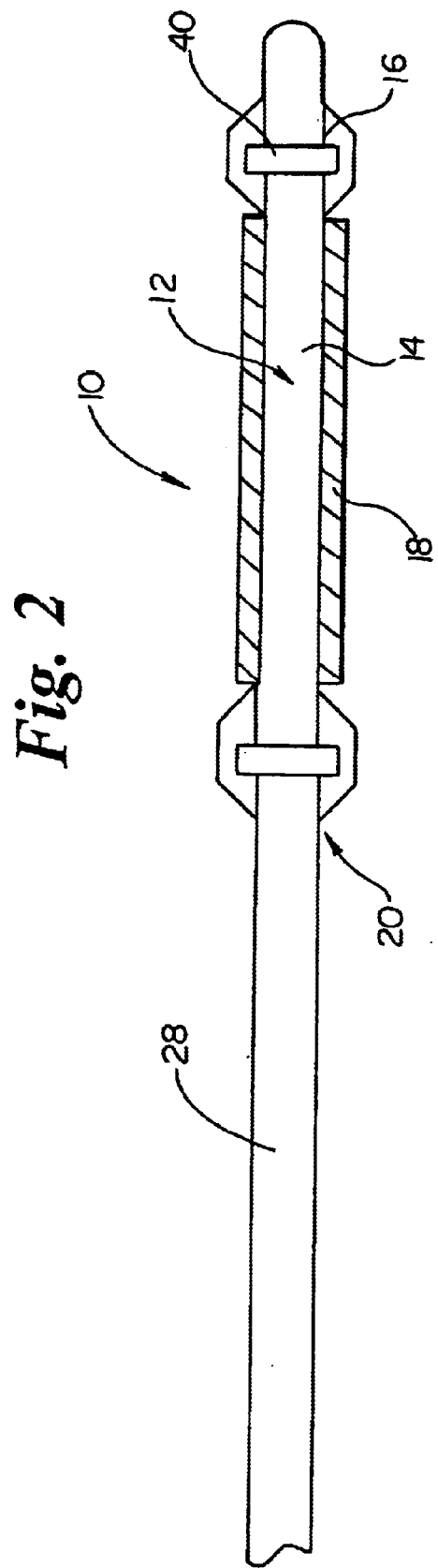
FIG. 2 is a side view of an embodiment of the invention wherein the balloon is depicted in a first inflation state.

As may be seen in FIGS. 2–5 the balloon 12 may be characterized as having at least two inflation states in addition to the first inflation state shown in FIG. 1. In FIG. 2, the balloon 12 is shown in the first inflation state; in FIGS. 3 and 6, the balloon 12 is respectively shown in alternative second inflation states, and in FIG. 5, the balloon 12 is shown in a third inflation state.

As may be seen in FIG. 2, when the balloon 12 is in the first inflation state, the catheter as a whole has a low profile sufficient for allowing the distal portion 20 of the catheter 10 to advance through a body lumen. In the first inflation state the stent mounting region 14 of the balloon 12 will typically have a diameter less than about 2.5 mm. The diameter of the stent mounting region may also range from about 1.5 mm to about 2.5 mm. In the first inflation state, the diameter of the end region(s) 16 will be greater than the diameter of the stent mounting region 14. The end region(s) 16 will typically be between about 1.65 mm to about 2.65 mm in diameter depending on the diameter of the stent mounting region 14.

The balloon 12 is inflated by injecting a fluid or other inflation means into the balloon 12. Typically the catheter 10 will be equipped with one or more inflation lumens (not shown) which are in fluid communication with the balloon and the proximal end of the catheter (not shown). Lumens as well as inflation means for balloons, including the present catheter balloon are well known in the art.

It may also be seen that in the embodiment shown in FIG. 2, the catheter 10 is equipped with marker bands 40. Marker bands may be used to denote the location of the stent on the catheter as well as to serve as a means of determining the location of the distal end of the catheter as it advances through the body. The marker bands are typically constructed of radiopaque materials. Examples of suitable marker bands are described in U.S. application Ser. No. 09/327,234 entitled *Radiopaque Bands* and filed Jun. 7, 1999, the entire contents of which being incorporated herein by reference.

As the balloon 12 is inflated, the balloon 12 will expand the stent 18. As may be seen in FIG. 3, the balloon 12 has been inflated to a second inflation or inflated state. In the second inflation state the balloon 12 may be configured to provide the stent mounting region 14 and the end regions 16 with substantially the same diameter such as is shown. However, in the embodiment illustrated in FIG. 4, when the balloon 12 is in the second inflation state, the diameter of the stent mounting region 14 remains less than the diameter of the end regions 16. In the second inflation state the diameter of the stent mounting region may range from about 3.0 to about 3.6 mm, in alternative embodiments however, the diameter may be less. Where the balloon is configured to have end regions 16 which have diameters greater than the diameter of the stent mounting region 14 the diameter of the end portions will typically be about 0.1 mm to about 1 mm greater than the diameter of the stent mounting region 14.

By providing the balloon 12 with end regions 16 that have a greater diameter than that of the stent mounting region 14, the end portions may be utilized to engage the ends 25 and 26 of the stent 18 thereby ensuring that the stent 18 does not migrate longitudinally relative to the balloon 12. By providing such enlarged end regions in both the first inflation state, such as is shown in FIG. 2 as well as in the second inflation state, such as is shown in FIG. 4, the position of the stent 18 remains constant on the balloon 12 during insertion and advancement of the catheter 10 as well as during balloon inflation.

Figure 3:
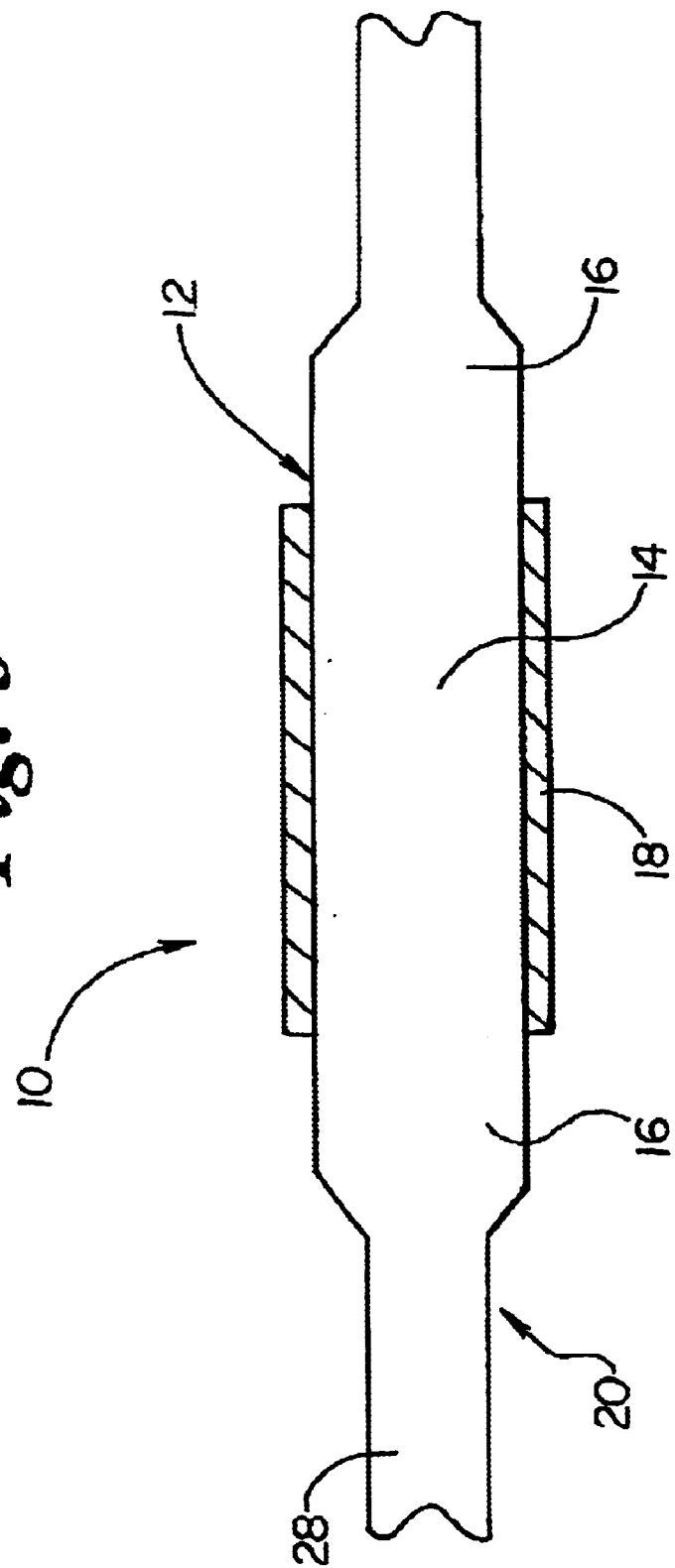
FIG. 3 is a side view of the embodiment of the invention shown in FIG. 2, wherein the balloon is depicted in the second inflation state.
Figure 4:
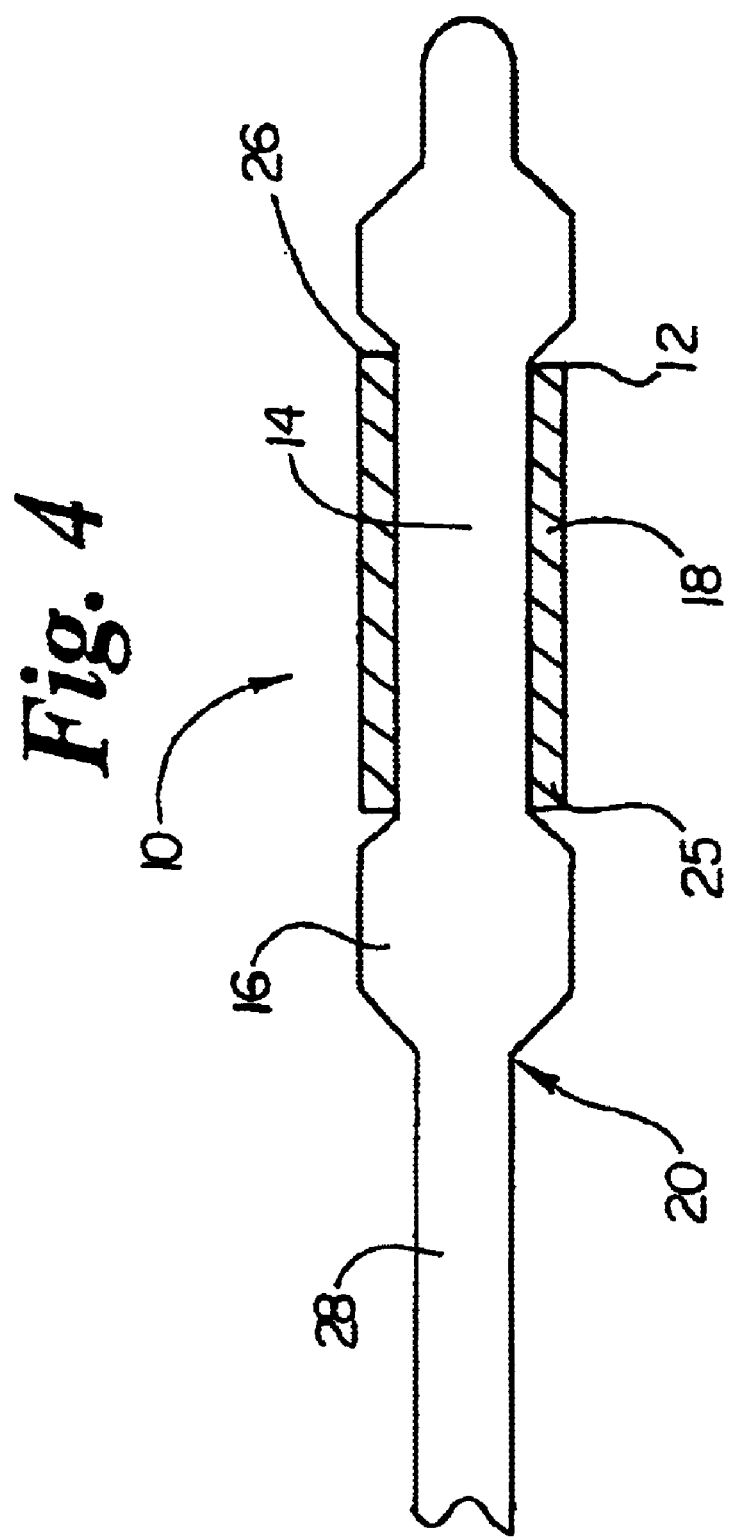
FIG. 4 is a side view of an alternative embodiment of the invention, wherein the balloon is depicted in the second inflation state.
Figure 5:
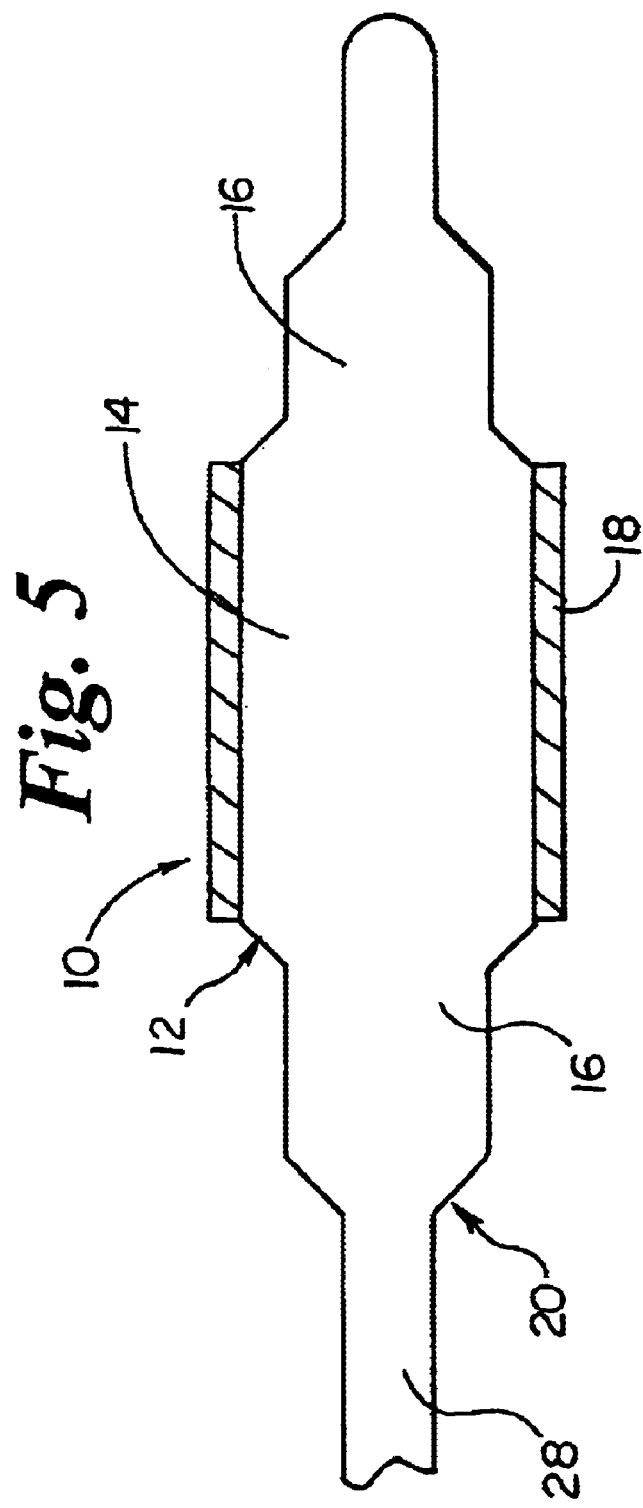
FIG. 5 is a side view of an embodiment of the invention wherein the balloon is shown in the third inflation state.

Subsequent to inflating the balloon 12 to a second inflation state, such as is shown in FIGS. 3 and 4, the balloon 12 may be further inflated to a third inflation state, such as is shown in FIG. 5.

As previously described the balloon 12 may be at least partially stepped compliant. In the embodiments discussed thus far the stent mounting region 14 is characterized as having a stepped compliance curve where as the adjacent end region(s) may be characterized as having a substantially linear compliance curve. Examples and description of a stepped compliant curves as well as a substantially linear compliance curve are described in U.S. Pat. No. 5,632,760 and U.S. Pat. No. 5,980,532, both of which are incorporated in their respective entireties herein by reference. Typically, a stepped compliance curve may be characterized by a first or low pressure segment defined by a low inflation pressure range. In the present invention, the low pressure segment of the stepped compliance curve of the stent mounting region 14 is generally collinear with a corresponding segment of the generally linear compliance curve of the end portions 16 which is defined by said low inflation pressure range. The stepped compliance curve of the stent mounting regions 16 may also include a transition segment during which the balloon expands rapidly relative to the at least one adjacent region and a high pressure segment during which the compliance curve of the stent mounting region expands slowly relative to the transition segment.

In the third inflation state the balloon 12 is inflated with pressure from about 12 to about 16 atmospheres. The greater pressure of the third inflation state corresponds to the high pressure segment of the compliance curve. The balloon 12 is constructed such that when the balloon 12 is inflated to the third inflation state, only the diameter of the stent mounting region 14 will continue to expand according to the high pressure segment of the stepped compliance curve. The diameter of the end regions 16 will exhibit only nominal expansion if at all when the balloon 12 is inflated to the third inflation state.

Alternatively, the balloon 12 may be characterized as having a stent mounting region 14 which has a higher rate of expansion than the rate of expansion of the end regions 16. Such that when the balloon 12 is inflated with a predetermined inflation pressure, the stent mounting region 14 will inflate to a greater degree than the end portions 16. Numerous methods could be applied to the balloon of the present invention to achieve different inflation rates. For example the end regions 16 could incorporate a relatively hard coating and/or additional materials such as the relatively stiff high pressure polymeric materials, such as thermoplastic polymers and thermoset polymeric materials, poly (ethylene terephthalate) (commonly referred to as PET), polyimide, thermoplastic polyimide, polyamides, polyesters, polycarbonates, polyphenylene sulfides, polypropylene and rigid polyurethanes. Such materials or coatings could be applied to a portion of the end region 16 to provide the region(s) 16 with a reduced rate of inflation relative to the stent mounting region 14. In addition, one or both expansion rates may also be characterized as being stepped compliant as described above.

Figure 6:
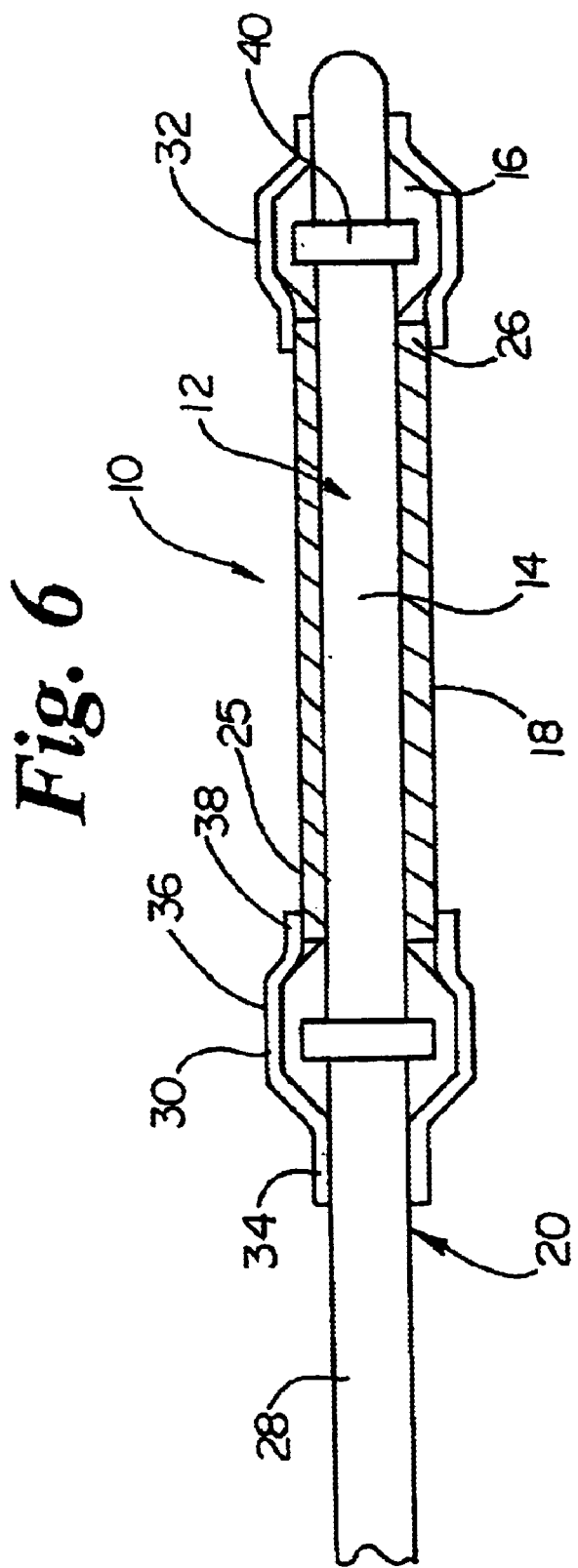
FIG. 6 is a side view of an embodiment of the invention which includes a pair of retractable stent retaining sleeves.

In an alternative embodiment shown in FIG. 6, the catheter 10 maybe equipped with retractable stent retaining sleeves 30 and 32. Each of the sleeves 30 and 32 have three portions: a catheter engagement potion 34, a balloon end region overlaying portion 36, and a stent end overlaying portion 38. The catheter engagement potion 34 is engaged to a portion of the catheter shaft 28 adjacent to the balloon 12. The sleeves 30 and 32 maybe engaged to the catheter in any manner known. For example the sleeves may be frictionally engaged, adhesively bonded, chemically or heat welded or other wise attached to the catheter shaft 28. The end overlaying portion 36 of each sleeve is slidingly disposed about the end region 16 of the balloon 12. The stent end overlaying region 38 of each sleeve 30 and 32, extends on to the stent mounting region 14 of the balloon 12 and respectively overlays stent ends 25 and 26. The stent end overlaying region 38 of each sleeve 30 and 32 retains the stent 18 on the stent mounting region 14 of the balloon 12 prior to stent delivery.

Figure 7:
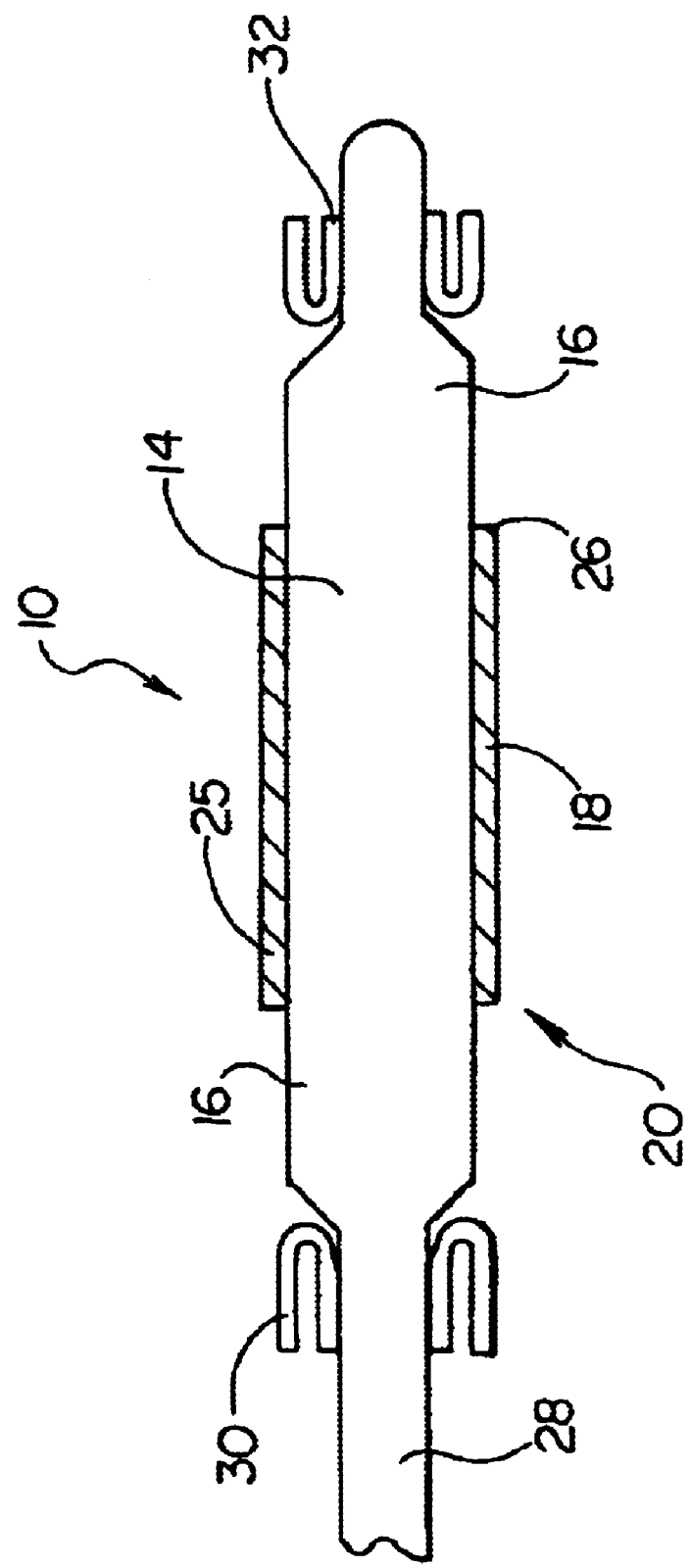
FIG. 7 is a side view of the embodiment of the invention shown in FIG. 6 wherein the balloon is in the second inflation state and the sleeves are retracted.

As may be seen in FIG. 7, when the balloon 12 is inflated to the second inflation state, the sleeves 30 and 32 are retracted off of the respective stent ends 25 and 26 to release the stent.

In the embodiments shown in FIGS. 3, 4 and 7, the balloon 12 may be inflated to the third inflation state as is shown in FIG. 5. In addition the sleeves 30 and 32 may be configured to retract off of the stent ends 25 and 26 when the balloon 12 is in the third inflation state rather than the second inflation state.

Figure 8:
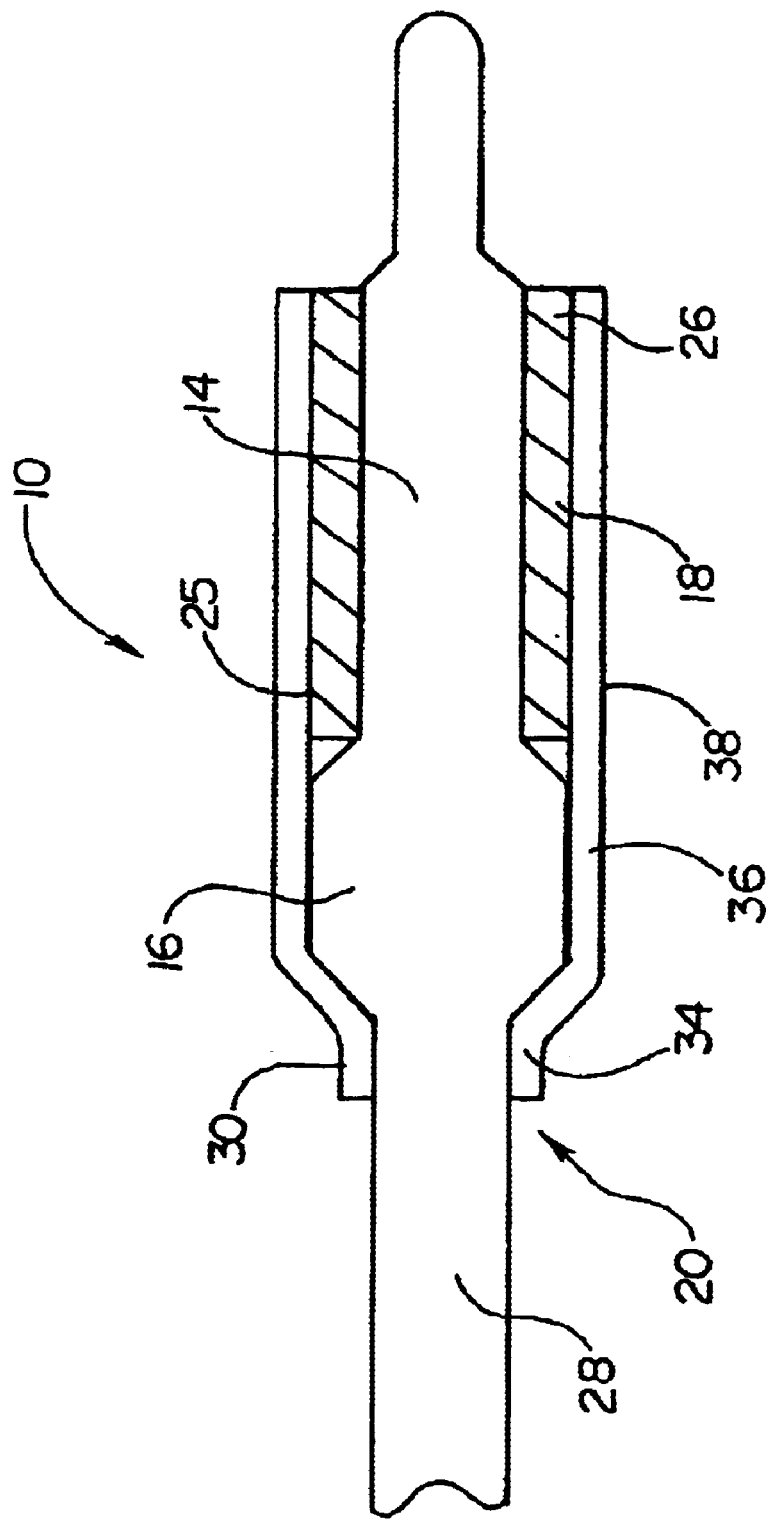
FIG. 8 is a side view of an embodiment of the invention which includes a single retractable stent retaining sleeve.

Alternatively, the catheter 10 may include a single sleeve 30 such as may be seen in FIG. 8.

Figure 9:
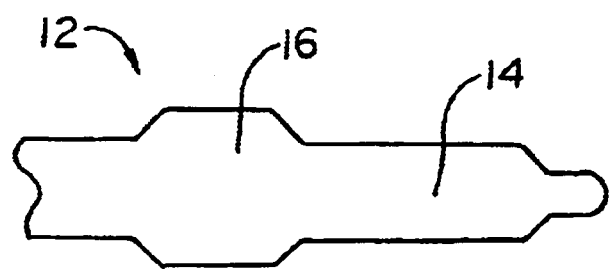
FIG. 9 is a side view of the balloon shown in FIG. 8 shown in the first inflation state.
Figure 10:
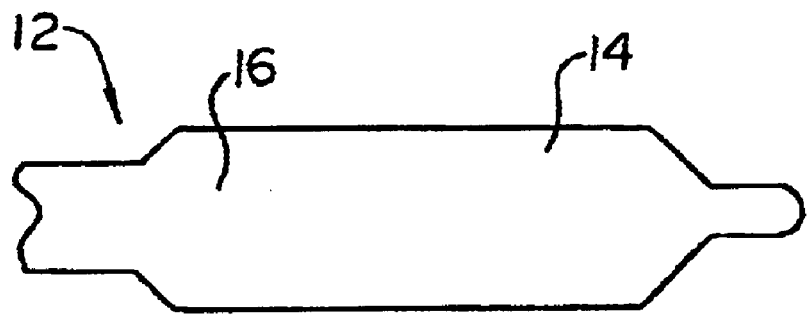
FIG. 10 is a side view of the balloon shown in FIG. 9 shown in the second inflation state.
Figure 11:
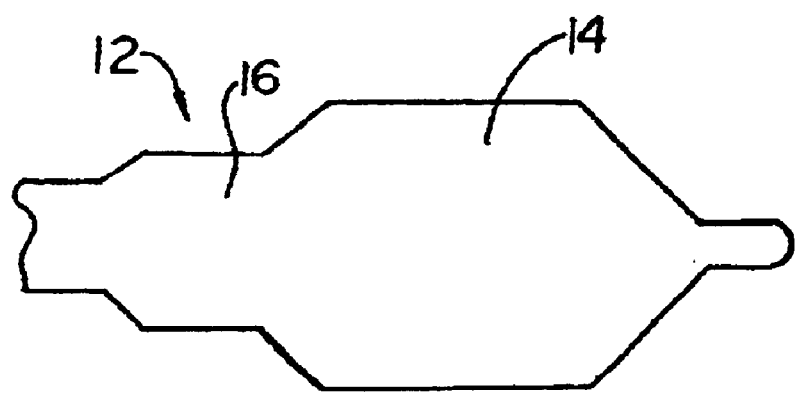
FIG. 11 is a side view of the balloon shown in FIG. 10 shown in the third inflation state.

In another alternative embodiment of the invention that may be seen in FIGS. 9–11, the invention may be directed exclusively to the inventive balloon 12 such as the balloon 12 shown in FIG. 1. In the present embodiment, the balloon 12 is shown with a stent mounting region 14 distally adjacent to a single end portion 16, such as may also be seen in FIG. 8. In FIGS. 9–11 the balloon 12 is shown respectively in the first inflation state, the second inflation state and the third inflation state. The balloon 12 may be incorporated into a balloon catheter or a stent delivery catheter such as those previously shown and described above, or as may be known in the art.

Figure 12:
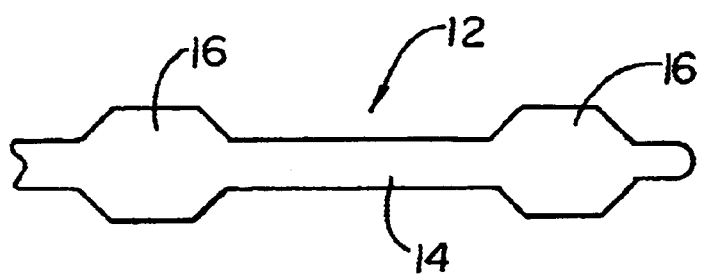
FIG. 12 is a side view of an embodiment of the balloon shown in the first inflation state.
Figure 13:
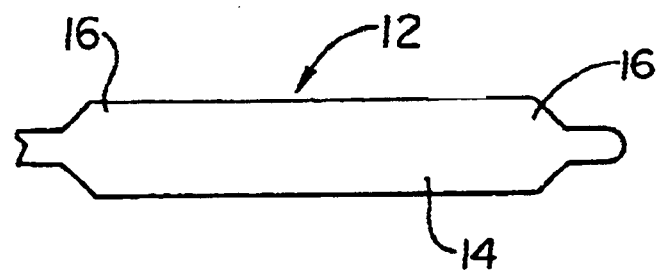
FIG. 13 is a side view of the balloon shown in FIG. 12 shown in the second inflation state.
Figure 14:
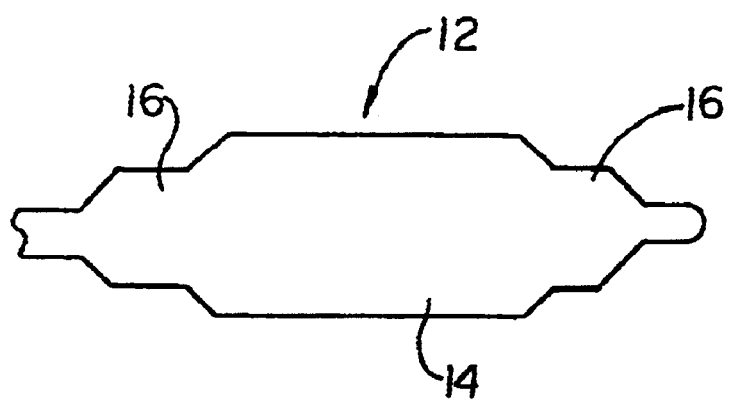
FIG. 14 is a side view of the balloon shown in FIG. 13 shown in the third inflation state.

Similar to the embodiments shown in FIGS. 9–11, the alternative embodiments shown in FIGS. 12–14 are directed to the balloon 12 portion of the catheter such as is shown in FIGS. 2–4 above. In the embodiments shown in FIGS. 12–14, the balloon 12 has a distal adjacent end 16 and a proximal adjacent end 17 which surround the stent mounting region 14. As with the previous embodiments, the embodiments shown in FIGS. 12–14 may be incorporated into any type of balloon catheter or stent delivery catheter especially those described herein. The balloon 12 of FIGS. 9–14 may include the same inflation characteristics as the balloons 12 of the various embodiments of the invention previously described.

In all of the embodiments described herein, if a stent is utilized with the balloon 12 the stent may be deployed from the second inflation state by simply collapsing the balloon subsequent to achieving the second inflation state, such as is depicted in FIGS. 3, 4 and 7. However, the stent may be further expanded by inflating the balloon 12 to the third inflation state. By further expanding the stent 18 in this manner the balloon 12 may be used to predilate a vessel by expanding to the second inflation state, and then seating the stent in place by expanding the balloon 12 to the third inflation state such as is shown in FIG. 5.

The balloon 12 of the various embodiments discussed herein should be made of a thermoplastic polymer material which has a high strength, and gives a low compliance balloon at pressures above about 15 atmospheres. For purposes of this application "low compliance" is considered to correspond to a diameter increase of no more than 0.1 mm per increased atmosphere of pressure, preferably less than 0.06 mm/atm. Suitably the balloon polymer is poly(ethylene terephthalate) (PET) of initial intrinsic viscosity of at least 0.5, more preferably 0.7–0.9. Other high strength polyester materials, such as poly(ethylene napthalenedicarboxylate) (PEN), nylons such as nylon 11 or nylon 12, thermoplastic polyimides and high strength engineering thermoplastic polyurethanes such as Isoplast 301 sold by Dow Chemical Co., and Pebax™ (a block copolymer polyamide and polyether) made by Elf Atochem. are considered suitable alternative materials. Desirably the balloon is blown in a way which will give a wall strength of at least 18,000 psi, preferably greater than 20,000 psi. Techniques for manufacturing balloons with such wall strengths are well known.

After being blown, the stent mounting region 14 of the balloon 12 is provided with a stepped compliance curve by annealing the balloon for a short time after blowing at a pressure at or only slightly above ambient and at a temperature which causes the blown balloon to shrink. The process is described in U.S. Pat. No. 5,348,538, incorporated in its entirety herein by reference. However, the balloons of the invention are desirably constructed with a greater difference between the low pressure and high pressure linear regions of the compliance curve so that the transition between the two regions results in a step-up of diameter of the balloon of at least 0.4 mm. This is accomplished by blowing the balloon to the larger diameter and then shrinking to a greater extent than was done in the specific illustrative examples of U.S. Pat. No. 5,348,538. The amount of shrinkage is controlled by the pressure maintained in the balloon during annealing and the temperature and time of the annealing. For a balloon made from 0.74 intrinsic viscosity PET, the blowing pressure is suitably in the range 200–400 psi, and temperature is suitably in the range of 90–100° C., and the annealing pressure is in the range of 0–20, preferably 5–10 psi at 90–100° for 3–10 seconds.

In a further aspect of the invention, the balloons employed in the inventive process are configured so that the stent mounting region 14 of the balloon 12 has a stepped compliance curve and the remainder of the balloon, specifically the end region(s) 16 have an unstepped or substantially linear compliance curve, the low pressure regions of the compliance curves of both the stent mounting region 14 and the end region(s) 16 being generally collinear.

The invention may also be practices by use of dual layer balloons such as described in co-pending U.S. application Ser. No. 08/243,473, filed May 16, 1994 as a continuation of now abandoned U.S. application Ser. No. 07/927,062, filed Aug. 8, 1992, incorporated herein by reference, and in U.S. Pat. No. 5,358,487, incorporated herein by reference. Suitably both balloons of the dual layer balloons are low compliance balloons designed with the outer balloon portion larger by at least 0.25 mm than the inner portion and the inner balloon designed to burst at a pressure below about 15 atm so that the compliance curve follows the inner balloon portion until it reaches burst diameter and then, after the inner balloon bursts, the outer balloon becomes inflated and can be expanded to a larger diameter than the burst diameter of the inner balloon.

Although the present invention has been described in terms of specific embodiments, it is anticipated that alterations and modifications thereof will no doubt be come apparent to those skilled in the art. It is therefore intended that the following claims be interpreted as covering all such alterations and modifications as fall within the true spirit and scope of the invention.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent delivery catheter, the catheter comprising:
   a catheter shaft, and
   a balloon, the balloon being mounted to the catheter shaft, the balloon when unconstrained being inflatable to a first inflation state at a first pressure where the balloon is nominally inflated by unfolding without substantial expansion and to a second inflation state at a second pressure higher than the first pressure, the balloon having a stent mounting region, at least one adjacent region, and at least one cone region, the at least one adjacent region being positioned between the stent mounting region and the at least one cone region, the stent mounting region having a stent mounting region inner diameter and the at least one adjacent region having an adjacent region inner diameter;
   wherein when the balloon is in the first inflation state the stent mounting region inner diameter is less than the adjacent region inner diameter, and when the balloon is in the second inflation state the stent mounting region inner diameter is substantially the same as the adjacent region inner diameter.

2. The stent delivery catheter of claim 1 further comprising a stent, the stent being disposed about at least a portion of the stent mounting region, the stent being expandable from an unexpanded state to a first stent expanded state, the stent further comprising a stent center, a first stent end and a second stent end.

3. The stent delivery catheter of claim 2 further comprising a stent retaining sleeve, the stent retaining sleeve having a stent retaining portion removingly disposed about at least one end of the stent and a catheter engagement portion engaged to a portion of the catheter shaft adjacent to the balloon.

4. The stent delivery catheter of claim 2 further comprising a first stent retaining sleeve and a second stent retaining sleeve, the first stent retaining sleeve having a stent retaking portion removingly disposed about the first stent end and a catheter engagement portion engaged to a first portion of the catheter shaft, the second stent retaining sleeve having a stent retaining portion removingly disposed about the second stent end and a catheter engagement portion engaged to a second portion of the catheter shaft.

5. The stent delivery catheter of claim 4 wherein when the balloon is expanded from the first inflation state to the second inflation state the stent is expanded from the unexpanded state to the first stent expanded state.

6. A stent delivery catheter, the catheter comprising:
   a catheter shaft;
   a balloon, the balloon being mounted to the catheter shaft, the balloon being inflatable to a first inflation state and to a second inflation state, the balloon having a stent mounting region, at least one adjacent region, and at least one cone region, the at least one adjacent region being positioned between the stent mounting region and the at least one cone region, the stent mounting region having a stent mounting region diameter, the at least one adjacent region having an adjacent region diameter and the at least one cone region having a cone region diameter, the balloon having an inflation curve wherein when the balloon is in the first inflation state the stent mounting region diameter is less than the adjacent region diameter, in the second inflation state the stent mounting region diameter is substantially the same as the adjacent region diameter, in both the first inflation state and the second inflation state the cone region diameter is less than the adjacent region diameter;
   a stent, the stent being disposed about at least a portion of the stent mounting region, the stent being expandable from an unexpanded state to a first stent expanded state, the stent further comprising a stent center, a first stent end and a second stent end; and
   a first stent retaining sleeve and a second stent retaining sleeve, the first stent retaining sleeve having a stent retaining portion removingly disposed about the first stent end and a catheter engagement portion engaged to a first portion of the catheter shaft, the second stent retaining sleeve having a stent retaining portion removingly disposed about the second stent end and a catheter engagement portion engaged to a second portion of the catheter shaft;
   wherein when the balloon is expanded from the first inflation state to the second inflation state the stent is expanded from the unexpanded state to the first stent expanded state; and
   wherein the stent mounting region is characterized as having a stepped compliance curve and the adjacent region is characterized as having a substantially linear compliance curve, the stepped compliance curve being characterized by a low pressure segment defined by a low inflation pressure range, said low pressure segment being generally collinear with a corresponding segment of the generally linear compliance curve of the at least one adjacent region which is defined by said low inflation pressure range, a transition segment during which the balloon expands rapidly relative to the at least one adjacent region and a high pressure segment during which the compliance curve of the stent mounting region expands slowly relative to the transition segment.

7. The stent delivery catheter of claim 6 wherein when the balloon is inflated to the second inflation state the stent mounting region is expanded according to the transition segment of the stepped compliance curve.

8. The stent delivery catheter of claim 6 wherein when the balloon is inflated to the second inflation state the stent mounting region is expanded according to the low pressure segment of the stepped compliance curve.

9. The stent delivery catheter of claim 4 wherein when the stent is expanded from the unexpanded state to the first stent expanded state the first stent retaining sleeve is configured to retract off of the first stent end, the second stent retaining sleeve is configured to retract off of the second stent end thereby releasing the stent from the first and second stent retaining sleeves.

10. The stent delivery catheter of claim 1 wherein the balloon further comprises a third inflation state, in the third inflation state the stent mounting region diameter being greater than the adjacent region diameter.

11. The stent delivery catheter of claim 10 further comprising a stent, the stent being disposed about at least a portion of the stent mounting region, the stent being expandable from an unexpanded state to a first stent expanded state and to a second stent expanded state, wherein when the balloon is expanded to the third inflation state the stent is expanded to the second stent expanded state.

12. The stent delivery catheter of claim 6 wherein the balloon further comprises a third inflation state, in the third inflation state the stent mounting region diameter being greater than the adjacent region diameter.

13. The stent delivery catheter of claim 12 wherein when the balloon is inflated to the third inflation state the stent mounting region is expanded according to the transition segment of the stepped compliance curve.

14. The staff delivery catheter of claim 12 wherein when the balloon is inflated to the third inflation state the stent mounting region is expanded according to the high pressure segment of the stepped compliance curve.

15. The stent delivery catheter of claim 1 wherein when the balloon is in the first inflation state the stent mounting region diameter is about 1.5 mm to about 2.5 mm.

16. The stent delivery catheter of claim 1 wherein when the balloon is in the first inflation state the adjacent region diameter is about 1.65 mm to about 2.65 mm.

17. The stent delivery catheter of claim 1 wherein when the balloon is in the second inflation state the adjacent region diameter has a range of about 2.0 mm to about 3.75 mm.

18. The stent delivery catheter of claim 1 wherein when the balloon is in the third inflation state the stat mounting region diameter has a range of about 2.75 mm to about 4.25 mm and the adjacent region diameter has a range of about 2.0 mm to 3.75 mm.

19. The stent delivery catheter of claim 1 wherein the balloon is constructed from at least one member of the group consisting of: thermoplastic polyurethane, polyethylene, polyesters, poly(butylene terephthalate)-block-poly (tetramethylene oxide) polymers, polyetherether ketone, block copolymers of polyether polymers and polyamides, block copolymers of polyether and polyester polymers, polyamides, block polyimides, polytetrafluoroethylene, polyolefins, silicone elastomers, and any combinations thereof.

20. The stent delivery catheter of claim 19 wherein the balloon is at least partially constructed from PEBAN.

21. The stent delivery catheter of claim 10 wherein when the balloon is inflated to a first pressure oft atm to about 3 atm the balloon is in the first inflation state, when the balloon is inflated to a second pressure of more than about 3 atm to about 6 atm the balloon is in the first inflation state, when the balloon is inflated to a third pressure of about 12 atm to about 16 atm the balloon is in the third inflation stare.

22. The stent delivery catheter of claim 12 wherein when the balloon is inflated to a first pressure of greater than about 3 atm to about 6 atm the stent mounting region is in the low pressure segment of the stepped compliance curve and when the balloon is inflated to a third pressure of about 12 atm to about 16 atm the stent mounting region is in the high pressure segment of the stepped compliance curve.

23. The stent delivery catheter of claim 1 wherein the adjacent region further comprises a proximal adjacent region anti distal adjacent region.

24. A stent delivery catheter comprising:
a catheter shaft;
a balloon, the balloon being mounted to a distal portion of the catheter shaft, the balloon being inflatable to a first inflation state at a first pressure where the balloon is nominally inflated by unfolding without substantial expansion and to a second inflation state at a second pressure higher than the first pressure, the balloon having a stent mounting region, and a pair of balloon regions adjacent to the stoat mounting region, each of the balloon regions being positioned between the stent mounting region and a cone region of the balloon, the pair of balloon regions comprising:
a proximal adjacent region and a distal adjacent region, the stent mounting region having a stent mounting region diameter and each of the adjacent regions having an adjacent region diameter, in the first inflation state the stent mounting region diameter being less than the adjacent region diameter, in the second inflation state the stent mounting region diameter being no greater than the adjacent region diameter;
a stent, the stent being disposed about at least a portion of the stent mounting region, the stent being expandable from an unexpanded state to a first stall expanded state, the stent in the unexpanded state having an outer diameter less than or equal to the outer diameter of at least one of said adjacent regions in the first inflation state, the stent further comprising a stent center, a first stent end and a second stent end; and
a proximal stent retaining sleeve and a distal stent retaining sleeve, each of the stent retaining sleeves having a stent retaining portion and a catheter engagement portion, the stent retaining portion of the distal stent retaining sleeve being removingly disposed about the first stent end, the stent retaining portion of the proximal stent retaining sleeve being removably disposed about the second stent end, the catheter engagement portion of the distal stent retaining sleeve being engaged to a portion of the catheter shaft proximate to the distal adjacent region of the balloon, the catheter engagement portion of the proximal stent retaining sleeve being engaged to a portion of the catheter shaft proximate to the proximal adjacent region of the balloon, whereby when the balloon is inflated from the first inflation state to the second inflation state the at least one stent retaining sleeve is retracted off of the at least one end of the stent.

25. The stent delivery catheter of claim 24 wherein the stent mounting region of the balloon is characterized as having a stepped compliance curve.

26. The stent delivery catheter of claim 25 therein each of the adjacent regions of rite balloon are characterized as having a substantially linear compliance curve.

27. The stent delivery catheter of claim 24 wherein when the balloon is in the second inflation state the stent mounting region diameter is about 0.05 mm to about 0.25 mm less than the adjacent region diameter.

28. The stent delivery catheter of claim 24 wherein the balloon is further characterized as having a third inflation state, when the balloon is inflated to the third inflation state the stent mounting region diameter is greater than the adjacent region diameter.

29. The stent delivery catheter of claim 24 wherein when the balloon is in the third inflation state the stent mounting region diameter is about 0.05 mm to about 0.25 mm greater than the adjacent region diameter.

30. A stent delivery catheter comprising:
a catheter shaft;
a balloon, the balloon being mounted to a distal portion of the catheter shaft, the balloon being inflatable to a first inflation state, to a second inflation slate, and to a third inflation state, the balloon having a stent mounting region and a pair of adjacent end regions, the stent mounting region having a stent mounting region diameter and the pair of end regions each having an end region diameter, in the first inflation state the stent mounting region diameter being less that the end region diameter in the second inflation state the stent mounting region diameter being no greater than the end region diameter, in the third inflation state the stent mounting region diameter being greater than the end region diameter; and a stent, the stent being disposed about at least portion of the stent mounting region, the stent being expandable from an unexpanded state to an expanded state, the stent further comprising a stent center, a first stent end and a second stent end, the stent in the unexpanded state having an outer diameter less than or equal to the outer diameter of a balloon end region in the first inflation state.

31. The stent delivery catheter of claim 30 further comprising a pair of stent retaining sleeves, each of the stent retaining sleeves having:

a stent retaining portion removingly disposed about one of the ends of the stent, an end region overlaying portion and a catheter engagement portion engaged to a portion of the catheter shaft adjacent to the balloon, whereby when the balloon is inflated from the first inflation state to the second inflation state retaining sleeves are retracted off of the ends of the stent and the end regions of the balloon.

32. A stent delivery catheter comprising:

a catheter shaft;

a balloon, the balloon being mounted to a distal portion of the catheter shaft, the balloon being inflatable to a first inflation state, to a second inflation state, and to a third inflation state, the balloon having a stent mounting region and a pair of adjacent end regions, the stent mounting region having a stent mounting region diameter and the pair of end regions each having an end region diameter, in the first inflation state the stent mounting region diameter being less than the end region diameter, in the second inflation state the stent mounting region diameter being no greater than the end region diameter, in the third inflation state the stent mounting region diameter being greater than the end region diameter;

a stent, the stent being disposed about at least a portion of the stent mounting region, the stent being expandable from an unexpanded state to an expanded state, the stent further comprising a stent center, a first stent end and a second stent end; and a pair of stent retaining sleeves, each of the stent retaining sleeves having a stent retaining portion removingly disposed about one of the ends of the stent, an end region overlaying portion and a catheter engagement portion engaged to a portion of the catheter shaft adjacent to the balloon, whereby when the balloon is inflated from the first inflation state to the second inflation state the stent retaining sleeves are retracted off of the ends of the stent and the end regions of the balloon;

wherein when the balloon is in the first inflation state and the second inflation state the pair of end regions are engaged to the first stent end and the second stent end respectively, thereby preventing longitudinal movement of the stent relative to the balloon.

* * * * *